United States Patent [19]

Ding

[11] Patent Number: 5,980,972
[45] Date of Patent: Nov. 9, 1999

[54] METHOD OF APPLYING DRUG-RELEASE COATINGS

[75] Inventor: Ni Ding, Plymouth, Minn.

[73] Assignee: Schneider (USA) Inc, Plymouth, Minn.

[21] Appl. No.: 08/935,371

[22] Filed: Sep. 22, 1997

Related U.S. Application Data

[60] Provisional application No. 60/033,443, Nov. 20, 1996.

[51] Int. Cl.$^6$ .............................. B05D 1/34; B05D 1/18; B05D 1/02; A61L 27/00
[52] U.S. Cl. ..................... 427/2.24; 427/2.28; 427/336; 427/426; 427/430.1
[58] Field of Search .................................. 427/2.24, 426, 427/430.1, 245, 246, 336, 2.28

[56] References Cited

U.S. PATENT DOCUMENTS

| | | | |
|---|---|---|---|
| 3,932,627 | 1/1976 | Margraf | 424/183 |
| 4,292,965 | 10/1981 | Nash et al. | 128/260 |

(List continued on next page.)

FOREIGN PATENT DOCUMENTS

| | | |
|---|---|---|
| 0 621 015 A1 | 10/1994 | European Pat. Off. |
| 0623354 | 11/1994 | European Pat. Off. |
| 0 734721 A2 | 10/1996 | European Pat. Off. |
| WO 91/12779 | 9/1991 | WIPO |
| WO 92/15286 | 9/1992 | WIPO |
| WO 94/01056 | 1/1994 | WIPO |
| WO 94/21308 | 9/1994 | WIPO |
| WO 94/21309 | 9/1994 | WIPO |
| WO 94/24961 | 11/1994 | WIPO |
| PCT/IB 96/00272 | 6/1996 | WIPO |

OTHER PUBLICATIONS

Michael N. Helmus, "Grant Application–Ionic–Hydrophilic Density: Platelet/Monocyte Adherence" Dec. 1981–Dec. 1984, pp. 13, 14, and 26–31.

Mansoor Amiji and Kinam Park, "Surface Modification of Polymeric Biomaterials with Poly(Ethylene Oxide), Albumin, and Heparin for Reduced Thrombogenicity", Purdue University, School of Pharmacy, West Lafayette, IN, 47907. (no month or year).

Baxter Healthcare Corp. Duraflo Biocompatible Treatment 1995, no month.

Ludwig K. von Segesser, MD., "Heparin–Bonded Surfaces in Extracorporeal Membrane Oxygenation for Cardiac Support", The Society of thoracic Surgeons, (1996) no month.

Li–Chien Hsu, "Principles of Heparin–Coating Techniques", Perfusin 6: 209–219 (1991) no month.

J.M. Toomasian et al., "Evaluation of Duraflo II Heparin Coating in Prolonged Extracorporeal Membrane Oxygenation", Asaio Trans 34: 410–14 (1988) no month.

S.D. Tong et al., "Non–Thrombogenic Hemofiltration System for Acute Renal Failure Treatment", Asaio Trans. 38: M702–M706 (1992) Sep.

(List continued on next page.)

Primary Examiner—Diana Dudash
Attorney, Agent, or Firm—Pennie & Edmonds LLP

[57] ABSTRACT

The invention is directed to a method of applying drug-release coatings whereby a polymer can be dissolved in a first solvent (solvent A) to form a polymer system and a drug can be dissolved or suspended in a second solvent (solvent B) to form a drug system. The coating or layer of coating so formed comprises a substantially uniform combination of the drug and polymer. Solvent B can be the same as or different than solvent A. The coating can be applied on a stent body by separately spraying or dipping the polymer system and the drug system onto the devices. The coating can be accomplished by either applying the polymer and drug systems sequentially or simultaneously. In certain embodiments, a drug can be suspended in solvent B. In some cases, three or more systems can be utilized. For instance, a third system containing pure solvent A or B can smooth the coating surface, if the solvent of the third spraying system is compatible with the polymer matrix.

18 Claims, 11 Drawing Sheets

U.S. PATENT DOCUMENTS

| | | | |
|---|---|---|---|
| 4,592,920 | 6/1986 | Murtfeldt | 427/2.3 |
| 4,596,723 | 6/1986 | Kaufman et al. | 427/336 |
| 4,613,665 | 9/1986 | Larm | 536/20 |
| 4,835,003 | 5/1989 | Becker et al. | 427/336 |
| 4,872,867 | 10/1989 | Joh et al. | 604/269 |
| 4,886,062 | 12/1989 | Wiktor | 128/343 |
| 4,916,193 | 4/1990 | Tang et al. | 525/413 |
| 4,917,686 | 4/1990 | Bayston et al. | 604/265 |
| 4,994,071 | 2/1991 | McGregor | 606/194 |
| 5,011,694 | 4/1991 | Nuernberg et al. | 427/336 |
| 5,053,048 | 10/1991 | Pinchuk | 623/1 |
| 5,061,275 | 10/1991 | Wallsten et al. | 623/1 |
| 5,092,877 | 3/1992 | Pinchuk | 623/1 |
| 5,163,952 | 11/1992 | Froix | 623/1 |
| 5,180,366 | 1/1993 | Woods | 604/96 |
| 5,182,317 | 1/1993 | Winters et al. | 523/112 |
| 5,185,408 | 2/1993 | Tang et al. | 525/415 |
| 5,221,698 | 6/1993 | Amidon et al. | 427/336 |
| 5,226,913 | 7/1993 | Pinchuk | 623/1 |
| 5,229,045 | 7/1993 | Soldani | 427/245 |
| 5,242,391 | 9/1993 | Place et al. | 604/60 |
| 5,258,020 | 11/1993 | Froix | 623/1 |
| 5,262,451 | 11/1993 | Winters et al. | 523/112 |
| 5,292,802 | 3/1994 | Rhee et al. | 525/54.1 |
| 5,304,121 | 4/1994 | Sahatjian | 604/53 |
| 5,308,889 | 5/1994 | Rhee et al. | 525/54.1 |
| 5,338,770 | 8/1994 | Winters et al. | 523/113 |
| 5,342,348 | 8/1994 | Kaplan | 604/891.1 |
| 5,342,628 | 8/1994 | Picha | 424/484 |
| 5,356,433 | 10/1994 | Rowland et al. | 623/1 |
| 5,380,299 | 1/1995 | Fearnot et al. | 604/265 |
| 5,415,619 | 5/1995 | Lee et al. | 600/36 |
| 5,419,760 | 5/1995 | Narciso, Jr. | 604/8 |
| 5,429,618 | 7/1995 | Keogh | 604/266 |
| 5,447,724 | 9/1995 | Helmus et al. | 424/426 |
| 5,449,382 | 9/1995 | Dayton | 523/1 |
| 5,456,940 | 10/1995 | Funderburk | 427/2.1 |
| 5,464,650 | 11/1995 | Berg et al. | 427/2.3 |
| 5,498,447 | 3/1996 | Nishi | 427/213 |
| 5,500,013 | 3/1996 | Buscemi et al. | 623/1 |
| 5,500,161 | 3/1996 | Andiranov et al. | 264/11 |
| 5,545,208 | 8/1996 | Wolff et al. | 623/1 |
| 5,551,954 | 9/1996 | Buscemi et al. | 623/1 |
| 5,578,075 | 11/1996 | Dayton | 623/1 |
| 5,605,696 | 2/1997 | Eury et al. | 424/423 |
| 5,624,411 | 4/1997 | Tuch | 604/265 |
| 5,637,113 | 6/1997 | Tartaglia et al. | 623/1 |
| 5,716,981 | 2/1998 | Hunter et al. | 514/449 |
| 5,725,567 | 3/1998 | Wolff et al. | 623/1 |
| B1 4,655,771 | 4/1987 | Wallsten | 623/1 |
| B1 4,954,126 | 9/1990 | Wallsten | 600/36 |

OTHER PUBLICATIONS

Bergstrom, Reduction of fibrinogen adsorption on PEG–coated polystyrene surfaces, 1992, p. 779–790, Baxter Healthcare Corp. Duraflo Biocompatible Treatment no month.

Michael N. Helmus, "Medical Device Design—A Systems Approach: Central Venous Catheters", (1990) Nov.

Polysciences Inc., TDMAC–Heparin Coatings, Nov. 1988, Data Sheet #172.

Barbucci, et al., Coating of Commercially available materials with a new heparinizable material, 1991, pp. 1259–1274 (no month).

Dennis E. Chenoweth, Complement Activation in Extracorporeal Circuits, pp. 306–329 (no month).

Jeffrey A. Hubbell, Ph.D., Jul.–Sep. 1993 Pharmacologic Modification of Materials, 121S–127S Sep.

Glenn P. Gravles, MD, Heparin–Coated Cardiopulmonary Bypass Circuits, Journal of Cardiothoracic and Vascular Anesthesia, vol. 8, No. 2, Apr. 1994, pp. 213–222.

K. Isihara, H. Hanyuda, and N. Nakabayashi, Synthesis of phospholipid polymers having a urethane bond . . . , Biomaterials, 1995, pp. 873–879 Jul.

J. Sanchez, G. Elgue, J. Riesenfeld and P. Olsson, Control of Contact activiation on end–point immobilized heparin, The role of antithrombin and the specific antithrombin–binding sequence, 1995, pp. 655–661, Journal of Biomedical Materials Research (no month).

Cardiology Conference European Society of Cardiology Conference Clinica, Sep. 4, 1995, pp. 24–26.

5,980,972

METHOD OF APPLYING DRUG-RELEASE COATINGS

This application claims priority to U.S. Provisional Application Ser. No. 60/033,443 filed Dec. 20, 1996.

FIELD OF THE INVENTION

This invention relates generally to drug-releasing coatings for medical devices which are inserted or implanted into the body. More particularly, the invention is directed to a method for applying drug-releasing coatings to medical devices in which a polymer is dissolved in a first solvent (solvent A) to form a polymer system and a drug is dissolved in a second solvent (solvent B) to form a drug system.

BACKGROUND OF THE INVENTION

In prior art methods, a composition comprising a mix of a drug and a polymer in a solvent is applied to the device to form a substantially uniform layer of drug and polymer; i.e. a layer in which the drug is dispersed in the polymer in a substantially uniform manner. Depending upon the types of polymers and drugs employed, finding a common solvent for these two constituents can be problematic. Where a common solvent for the drug and polymer is not available, attempts have been made to micronize the drug into small particles so that it can be suspended in the polymer solution. However, micronization can be time consuming, and may result in a loss of desired therapeutic properties of the drug. Therefore, a method of more easily putting both the drug and polymer into solution to obtain a drug releasing coating for medical devices is needed. Also needed is a method of applying a drug/polymer coating without having to combine the drug and polymer in a common solution or suspension.

SUMMARY OF THE INVENTION

The methods disclosed herein apply generally to implantable prostheses, especially expandable prostheses such as balloon expandable stents and self-expanding stents. Stents coated according to this invention may be, for instance, plastically deformable or self-expanding. In certain embodiments, the methods avoid the necessity of micronizing a drug before it is applied to a stent. In other embodiments, drug particulates can be utilized. The present invention can also be used where there is no common compatible solvent for both the polymer and the drug.

Broadly, the invention relates to a method of applying drug-release coatings containing a drug and a polymer, in which the drug is distributed in the polymer in a substantially uniform manner. A polymer can be dissolved in a first solvent (solvent A) to form a polymer system substantially free of biologically active materials (e.g., less than about 1% by weight of the polymer) and a drug can be dissolved in a second solvent (solvent B) to form a drug system substantially free of polymers (e.g., less than about 1% by weight of the drug). Solvent B can be the same as or different than solvent A. Different solvents are generally used when the drug has very low solubility in the polymer solution and no common solvent would be found for both the drug and polymer. By applying the polymer system and drug system separately to the surface of the medical device, the method forms a composite of the polymer and drug, i.e., a distribution of the drug throughout a network of polymer. Such composite may be substantially homogenous. The method of the present invention avoids the need for micronizing the drug prior to mixing it with the polymer to form the composite of drug and polymer. Although the method provides a coating or a layer of a coating which comprises a composite of the drug and polymer, it avoids the need for mixing the drug and polymer in one solution before applying the coating to the device.

A coating can be applied on a device, particularly a stent, by separately spraying the polymer system and the drug system. Methods of coating stents are disclosed in U.S. patent application Ser. Nos. 08/424,884; 08/526,273; and 08/663,490. These documents are incorporated herein by reference in their entireties for all purposes. The coatings of the invention can be accomplished by either spraying the polymer and drug systems sequentially or simultaneously, as further described below.

Instead of applying the coating by spraying, the coating can also be placed onto the medical device by dipping. This latter method of applying the coating is especially useful for devices which are not conducive to being spray coated. Such devices include without limitation the inner lumen of a stent graft. Also, the coating may be applied by using a combination of spraying and dipping.

Depending upon the coating thickness desired, multi-step coatings may be applied. Depending upon the solvent volatility, a waiting period may be required during the spraying or dipping process, or heat may be applied through a heat gun, a heat lamp or a heat chamber to facilitate the evaporation of the solvent(s).

In certain embodiments, it is not necessary for a drug to be dissolved in solvent B. Fine particles can be mixed, preferably suspended, in the solvent, and the coating can be applied as described herein. In some cases, three or more systems can be utilized. For instance, a third spraying or dipping system containing pure solvent A or B can smooth the coating surface, if the solvent of the third system is compatible with the polymer matrix, or a third spraying or dipping system containing a second elutable agent such as a drug. Polyethylene glycol, sugar, salt in solvent (which can be same or different than solvents A and B), can be applied to the stent. The resulting drug release profile, where two or more drugs are applied, can result in the different drugs being released simultaneously or sequentially.

A suitable sequence according to this invention could be one application of a polymer solution, one application of a drug solution and one application of pure solvent. Alternatively, the sequence could be one application by spraying or dipping of polymer solution, one application of solvent and one application of a drug solution or suspension. Alternatively, the sequence could be three parallel spraying systems. The number of cycles in each operation could be half, one, two or more. It is appreciated that those skilled in the art will find numerous combinations of coating orders and sequences for dual or multiple coating systems without departing from the inventive concept. The coating system can be hand-operated or automated to achieve different combinations.

DETAILED DESCRIPTION OF THE INVENTION

Polymers suitable for the present invention will preferably be hydrophobic biostable elastomeric materials which do not degrade and which minimize tissue rejection. Furthermore, the materials are preferably ones which will undergo encapsulation by tissue adjacent to the stent implantation site. Polymers suitable for such coatings include silicones (e.g., polysiloxanes and substituted polysiloxanes), polyurethanes (including polycarbonate urethanes), thermoplastic elastomers in general, ethylene vinyl acetate copolymers, polyolefin elastomers, EPDM rubbers and polyamide elastomers. The above-referenced materials are considered hydrophobic with respect to the contemplated environment of the invention.

Non-limiting examples of other polymers which are suitable for use in the present invention include bioabsorbable polymers such as polylactic acid, polyglycolic acid, polycaprolactone, polylactic acid—polyethylene oxide copolymers, cellulose, and the like. Other non-limiting examples of polymers that are suitable for use in the present invention also include biostable plastic materials such as acrylic polymers and its derivatives, nylon, and polyesters.

Non-limiting examples of drugs suitable for use in the present invention include antithrobotics, anticoagulants, antiplatelet agents, thrombolytics, antiproliferatives, anti-inflammatories, agents that inhibit hyperplasia and in particular restenosis, smooth muscle cell inhibitors, antibiotics, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium) and tissue formation (neointimal tissue).

The drug used in the invention may or may not be micronized. When the drug is not micronized, the particle size of the drug can be greater than about 10 $\mu$m. When the drug is micronized, the drug particle size is preferably 5–12 $\mu$m and more preferably about 5 $\mu$m.

The devices suitable for the invention include without limitation a variety of medical devices such as catheters, shunts, stents (e.g. self expandable or balloon expandable vascular or non-vascular stents), heart valves, grafts, and artificial organs or prostheses. The devices may have polymeric, metallic or ceramic surfaces.

Figure 10:
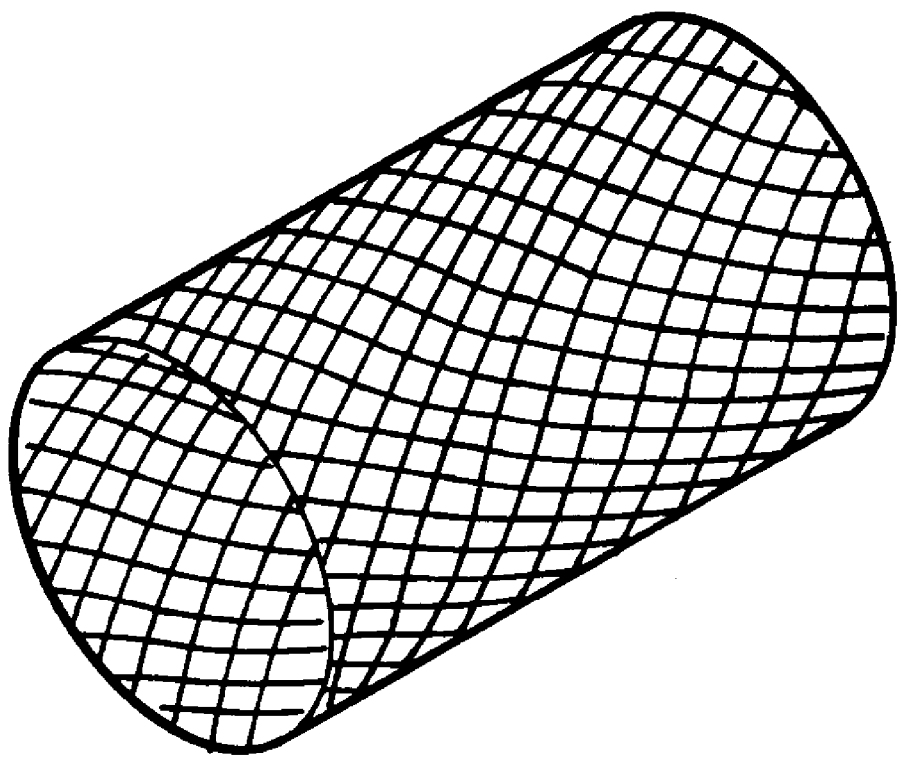
FIG. 10 shows a stent prior to coating.

The preferred materials for fabricating stents, particularly braided stents, such as that shown in FIG. 10, include metals such as stainless steel, tantalum, titanium alloys including nitinol (a nickel titanium, thermomemoried alloy material), DFT materials such as shown in U.S. Pat. No. 5,630,840 and certain cobalt alloys including cobalt-chromium-nickel alloys such as Elgiloy® and Phynox®. Bioabsorbable materials may also be used to form the stent structure, such as polylactic acid. Further details concerning the fabrication and details of other aspects of the stents themselves are found in U.S. Pat. Nos. 4,655,771 and 4,954,126 to Wallsten and U.S. Pat. No. 5,061,275 to Wallsten et al. which are incorporated herein by reference in their entireties.

Solvents which can be used in the present invention will preferably be compatible with the polymer or drug with which they are mixed. For instance, the polymer will preferably be fully dissolvable in the solvent with which it is mixed, and the drug will preferably be fully dissolvable in the solvent with which it is mixed. However, it is contemplated that certain embodiments of the present invention will include particulate drugs, such as heparin, mixed in solvent. Where drugs are in particulate form, the drug will preferably be suspended in the solvent. Non-limiting examples of solvents that can be used according to this invention include tetrahydrofuran, methanol, methyl ethyl ketone, chloroform, methylene chloride, acetonitrile, and water.

The following examples describe embodiments of the invention in which the coatings were applied to the medical devices by spray coating (Comparative Example and Examples 1–3) or by dip coating (Examples 4–6).

Comparative Example

Figure 1:
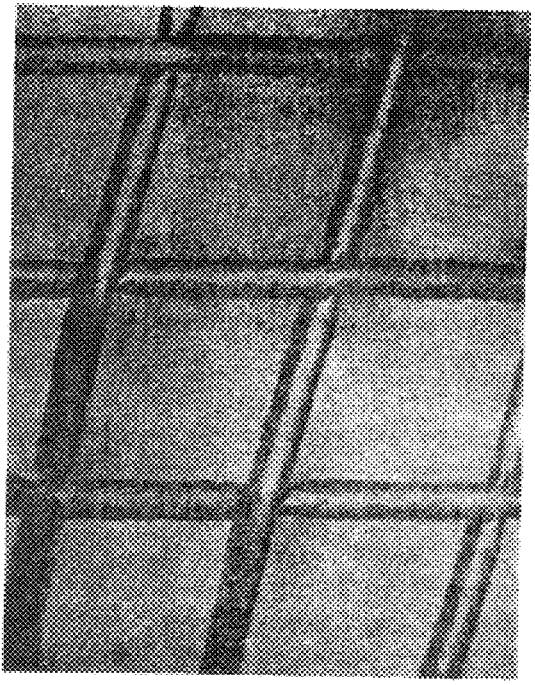
FIG. 1 is a photograph showing the results of the Comparative Example.
Figure 4:
FIGS. 4 and 5 are scanning electron microscope photographs showing the results of the Comparative Example in an unstressed state and a post-stressed state, respectively.
Figure 5:
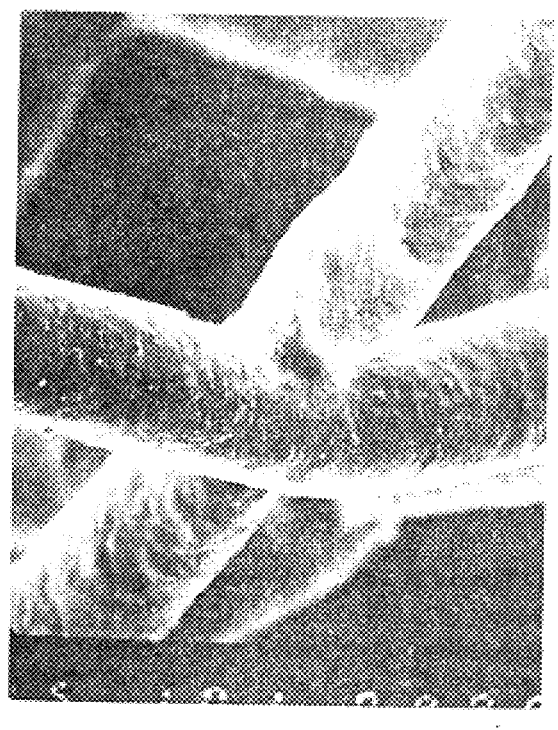

A silicone-xylene mixture (~34% solid weight from Applied Silicone Corporation) was weighed, and the solid silicone content was calculated. A ratio of $W_{dex}/W_{silicone\ solid}=0.1$ was used in the preparation. Here "dexi" or "DEX" refers to dexamethasone (Upjohn, Dexamethasone USP, CAS # 50-02-2). The volume amount of tetrahydrofuran (THF) (HPLC grade, Aldrich or EM Science) used was determined by multiplication of 20 with the weight of the solid silicone. DEX was first dissolved in THF and then transferred to a silicone-xylene mixture. A crosslinker agent was added and the solution was mixed well. A braided stent was coated by spraying multiple cycles of the homogeneous solution so prepared on the stent in an expanded state. The coated stent was then moved to a convection oven and cured at 150° C. for 45 minutes. It was then treated with argon gas plasma according to the procedure described in co-pending application Ser. No. 08/841,747, now U.S. Pat. No. 5,879,697. The results are shown in FIGS. 1, 4 and 5. FIGS. 1 and 4 are photographs of the coating in an unstressed state, i.e., before the stent was expanded or contracted. FIG. 5 is a photograph of the coating after the coated stent was mechanically stressed, i.e., following contraction and expansion of the stent.

EXAMPLE 1

Figure 2:
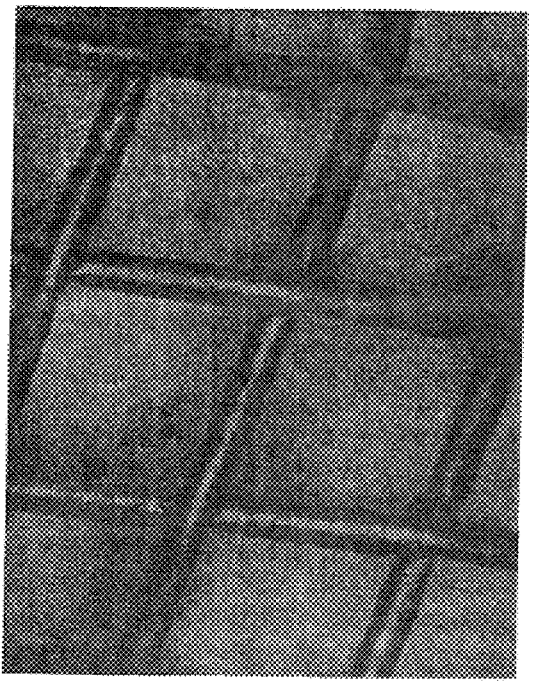
FIG. 2 is a photograph showing the results of Example 1.
Figure 6:
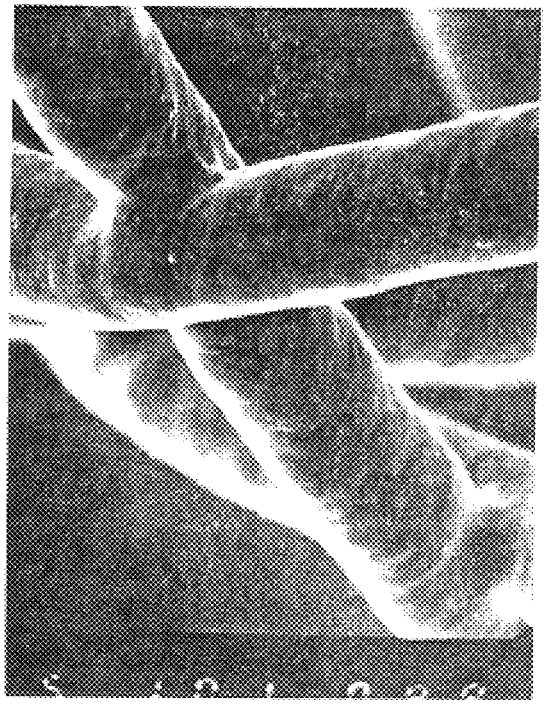
FIGS. 6 and 7 are scanning electron microscope photographs showing the results of Example 1 in an unstressed state and a post-stressed state, respectively.
Figure 7:
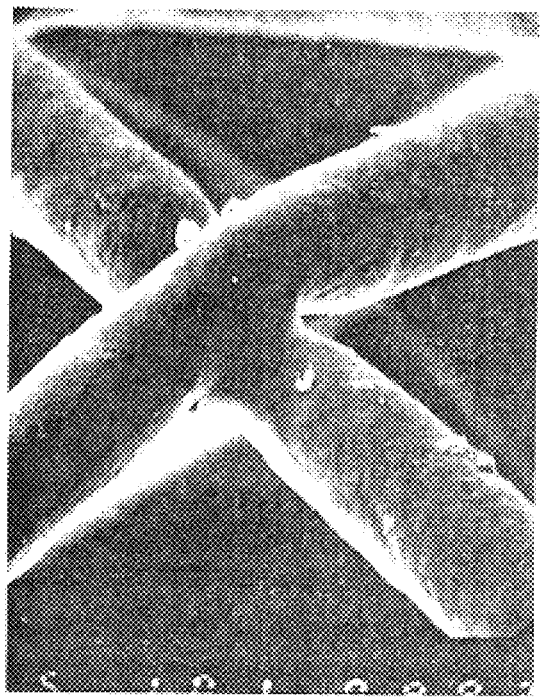

A 5% (w/w) solution of silicone solid in THF was prepared by adding the required THF and crosslinker agent into the silicone mixture. A separate 0.5% (w/w) solution of DEX in THF was prepared by adding THF into a beaker containing DEX. The ratio of $W_{dex}/W_{silicone\ solid}$ was 0.1. A badger 150-4 spray system was used with two reservoirs filled with two different solutions. The coating of the stent in an expanded state was accomplished by spraying one cycle of silicone solution, waiting for a short period of time (about 30 seconds), and spraying one cycle of DEX solution, waiting for a short period of time (about 30 seconds), and then repeating the spraying sequence. The very last spray cycle was silicone solution. For a coating thickness of 30 micron, about 30 cycles each were applied. The number of spray cycles used depended on the solution viscosity, the droplet size and the flow rate. The coated stent was then moved to a convection oven and cured at 150° C. for 45 minutes. It was then argon gas plasma treated. The results are shown in FIGS. 2, 6, and 7. FIGS. 2 and 6 are photographs of the coating in a unstressed state. FIG. 7 is a photograph of the coating after the coated stent was mechanically stressed.

EXAMPLE 2

Figure 3:
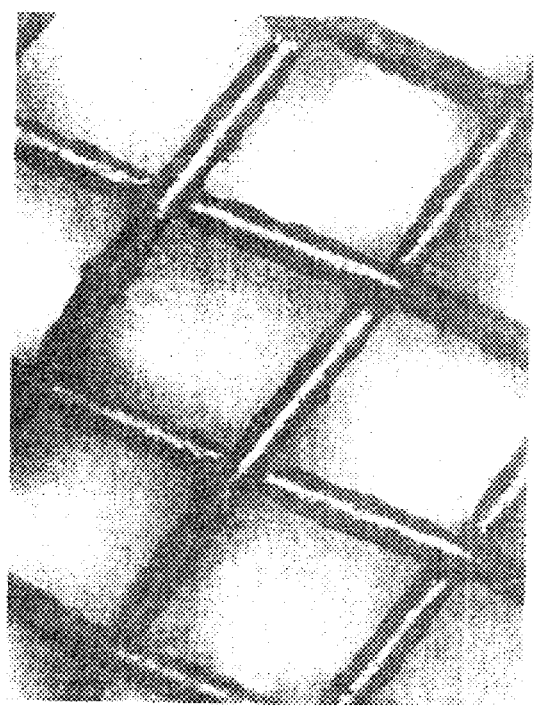
FIG. 3 is a photograph showing the results of Example 2.
Figure 8:
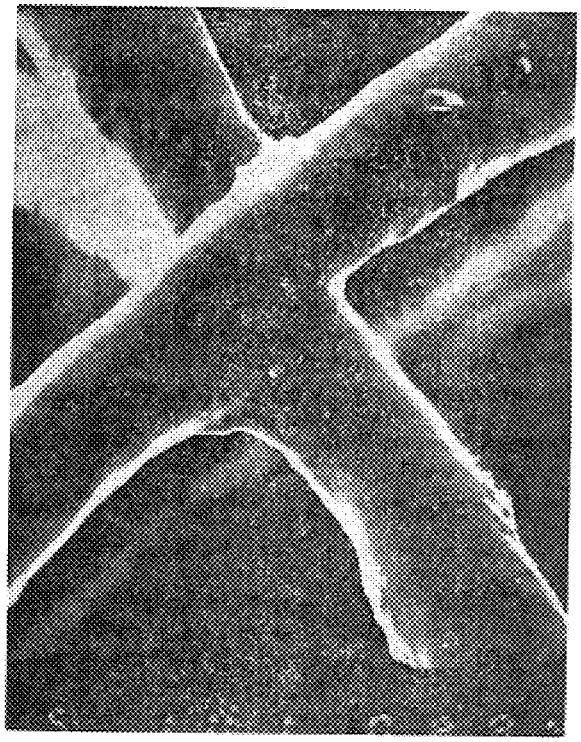
FIGS. 8 and 9 are scanning electron microscope photographs showing the results of Example 2 in an unstressed state and a post-stressed state, respectively.
Figure 9:

The process used to prepare this example was similar to the process utilized in Example 1 except that DEX was dissolved in methanol, which is a poor solvent for silicone. The ratio of $W_{dex}/W_{silicone\ solid}$ was maintained at 0.1 in the preparation. The results are shown in FIGS. 3, 8, and 9. FIGS. 3 and 8 are photographs of the coating in a unstressed state. FIG. 9 is a photograph of the coating after the coated stent was mechanically stressed, i.e., expanded and contracted.

EXAMPLE 3

Figure 15:
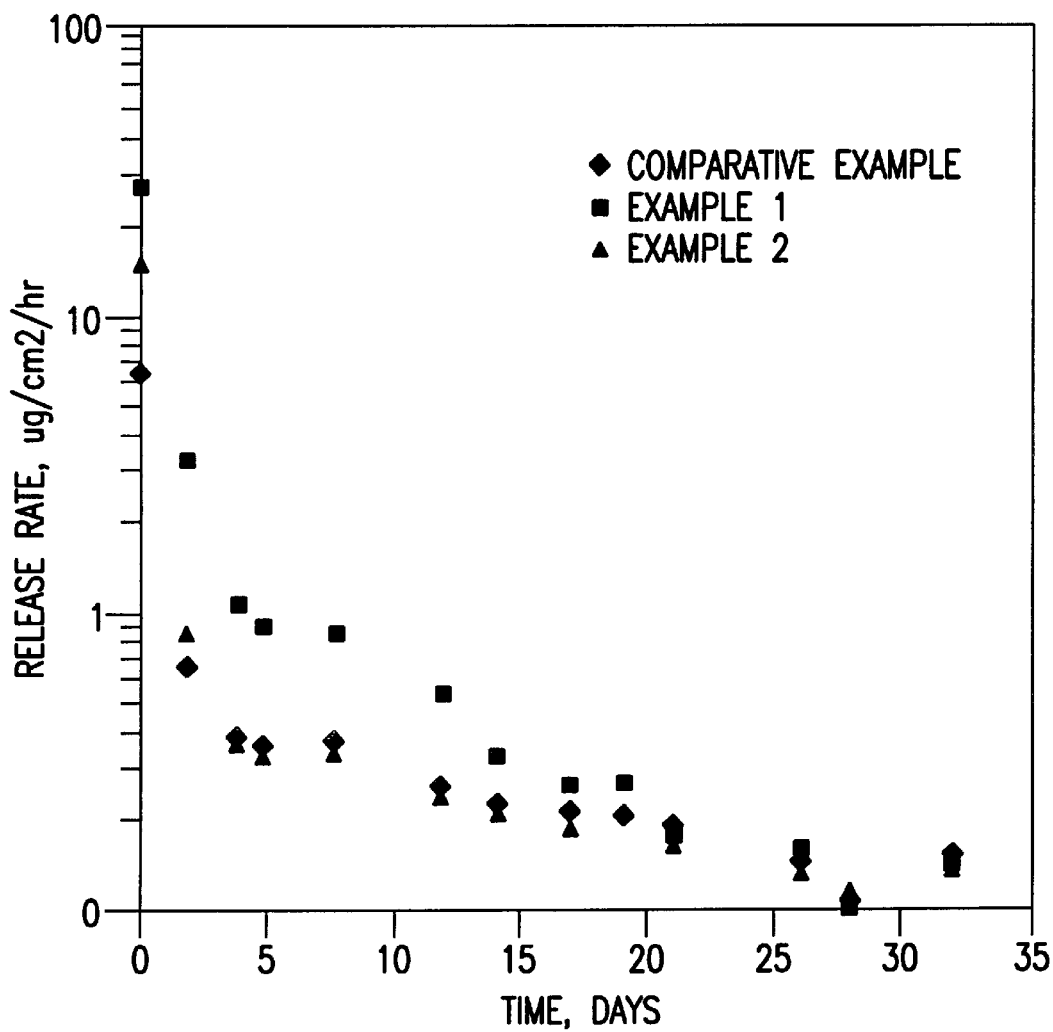
FIG. 15 graphically compares elution rates for the Comparative Example, Example 1 and Example 2.

The coated stents prepared in the Comparative Example, Example 1 and Example 2 were cut into 2 cm segments and put into 100 ml of polyethylene glycol (MW=400, Aldrich) and water mixture (40/60, v/v). The solution was changed frequently when sampling the solution. The DEX concentration was analyzed by using a Shimadzu high performance liquid chromatography instrument, operated with a UV detector at the wavelength of 254 nm. A C-8 column was used in the analysis. Table 1 and FIG. 15 show the DEX release data over one month for the coated stents. All three preparations in the Comparative Example, Example 1 and Example 2 prolonged the drug release and had similar release profiles.

TABLE 1

| | Release Rate Data ($\mu g/cm^2/hr$) | | |
|---|---|---|---|
| Time (days) | Comp. Ex. | Ex. 1 | Ex. 2 |
| 0.08 | 6.25 | 27.46 | 14.88 |
| 1.73 | 0.66 | 3.32 | 0.83 |
| 3.77 | 0.38 | 1.08 | 0.36 |
| 4.75 | 0.38 | 0.91 | 0.33 |
| 11.81 | 0.24 | 0.44 | 0.21 |
| 14.08 | 0.24 | 0.34 | 0.22 |
| 16.94 | 0.23 | 0.27 | 0.20 |
| 19.08 | 0.22 | 0.28 | 0.22 |
| 21.08 | 0.21 | 0.19 | 0.18 |
| 26.08 | 0.15 | 0.17 | 0.14 |
| 28.00 | 0.11 | 0.10 | 0.12 |
| 32.06 | 0.17 | 0.16 | 0.15 |

Figure 11:
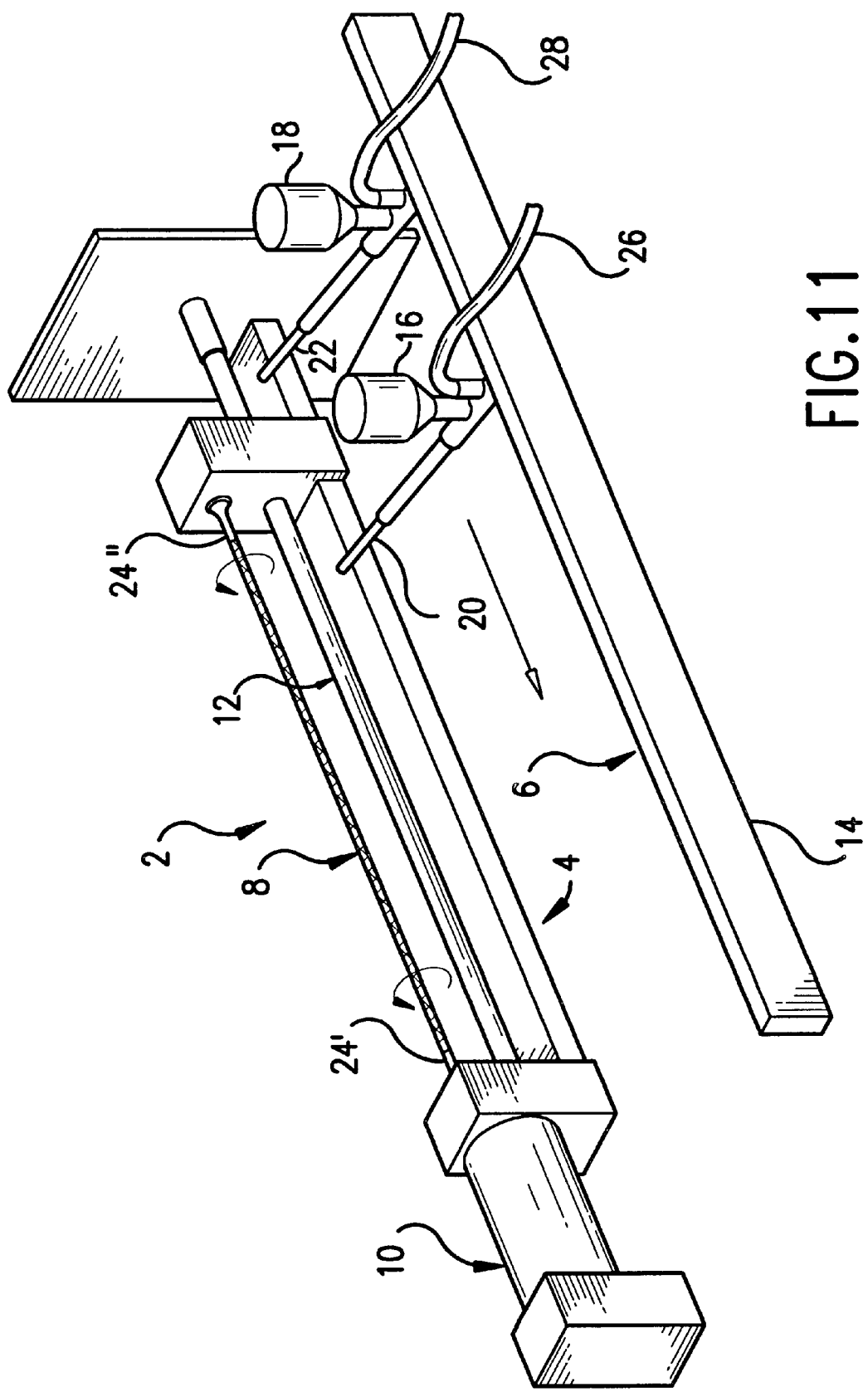
FIGS. 11 and 12 sequentially illustrate an embodiment of the present invention.
Figure 12:
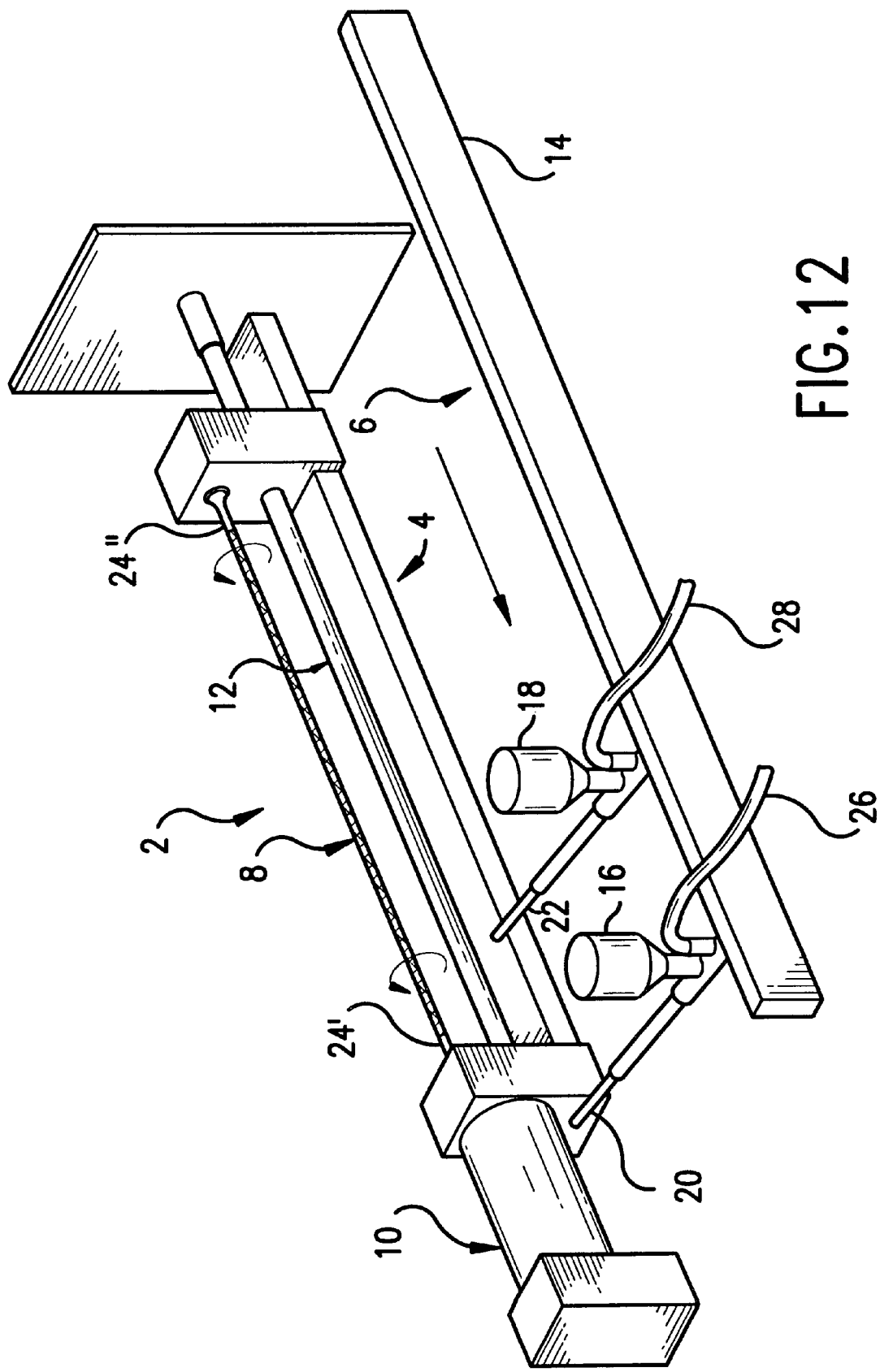

An embodiment of the present invention involving spray coating is sequentially illustrated in FIGS. 11 and 12. The drug-release coating apparatus 2 has a stent rotating element 4 and a spraying element 6.

A stent 8 is mounted on the stent rotating element 4 by clamping it at both ends to supporting rod elements 24', 24", which are typically alligator clamps. Preferably, stent 8 will be clamped in a position which is at least partially expanded or fully expanded such that its interior remains empty allowing spray coating to adhere to both the exterior and the interior surface of stent 8. Rod elements 24', 24" do not traverse the interior of stent 8. Motor 10 rotates the rod elements 24', 24" thereby rotating stent 8. Supporting rod 12 supports the stent rotating element 4.

Spraying element 6 has a structural support 14 on which a first spray canister 16 and a second spray canister 18 are mounted. First spray canister 16 is fluidly connected to first spray dispenser 20 and second spray canister 18 is fluidly connected to second spray dispenser 22. Gas supply means 26, 28 are connected to the spraying devices to provide gaseous means to propel the polymer and drug solutions.

The first and second spray canisters 16, 18 can be mounted on structural support 14 on a track (not shown) to enable longitudinal movement back and forth. In a simplified case, a hand can act as a support 14. In this embodiment, canisters 16, 18 are fixed at a predetermined distance from one another, so that they move to and from equidistant from one another. The hollow arrow in FIG. 11 shows canisters 16, 18 prior to leftward movement. Spray will begin once spray dispensers 20, 22 oppose the stent 8. The solid arrow in FIG. 12 shows canisters 16, 18 beginning their course back to the right, again beginning to spray once dispensers 20, 22 oppose the stent. This sequence can be repeated multiple times, as desired.

In this embodiment, first spray canister 16 can hold polymer in solvent and be free of drug, while second spray canister 18 can hold drug in solvent and be free of polymer, or vice versa.

Figure 13:
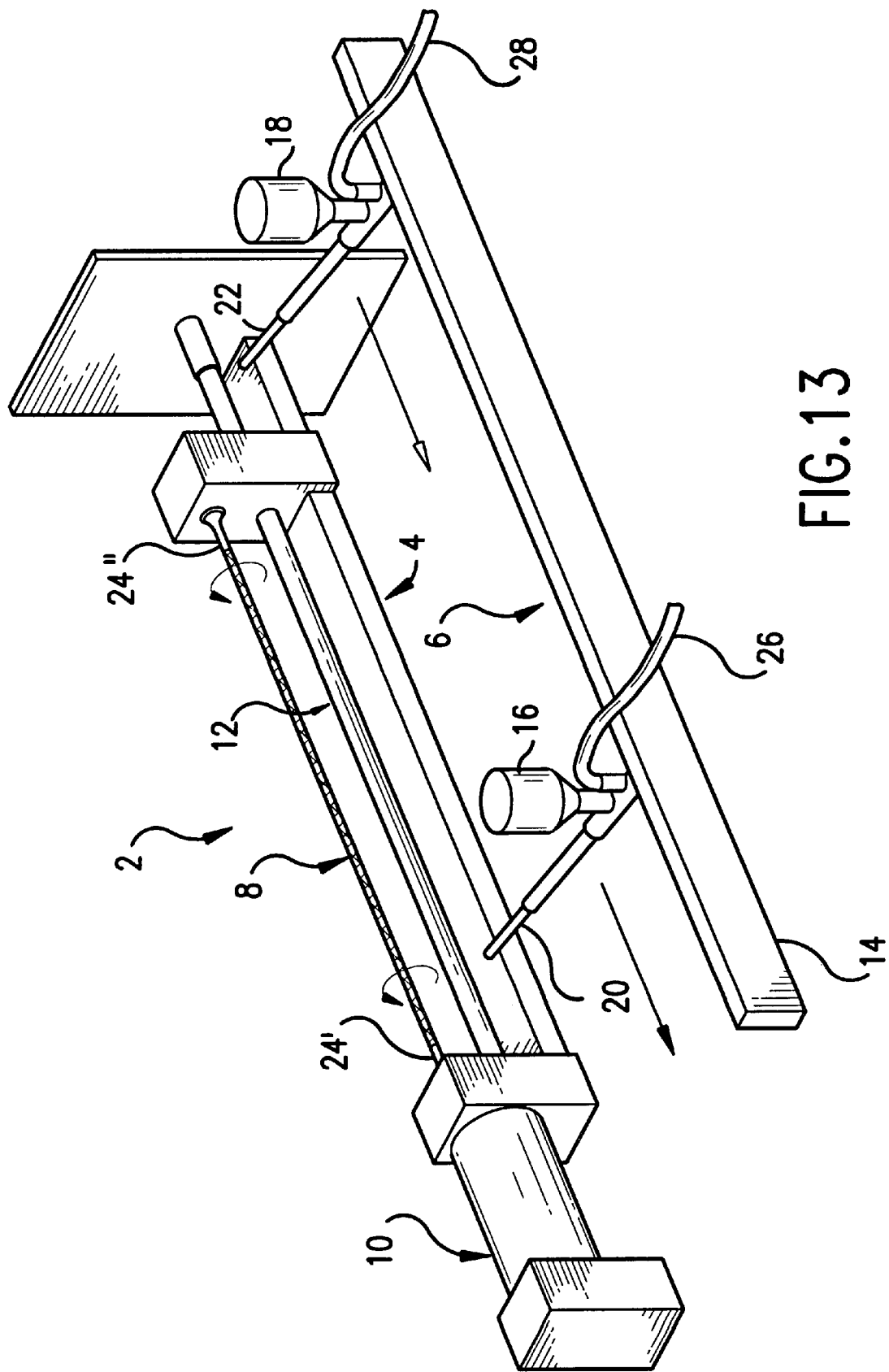
FIGS. 13 and 14 sequentially illustrate an alternative embodiment of the present invention.
Figure 14:
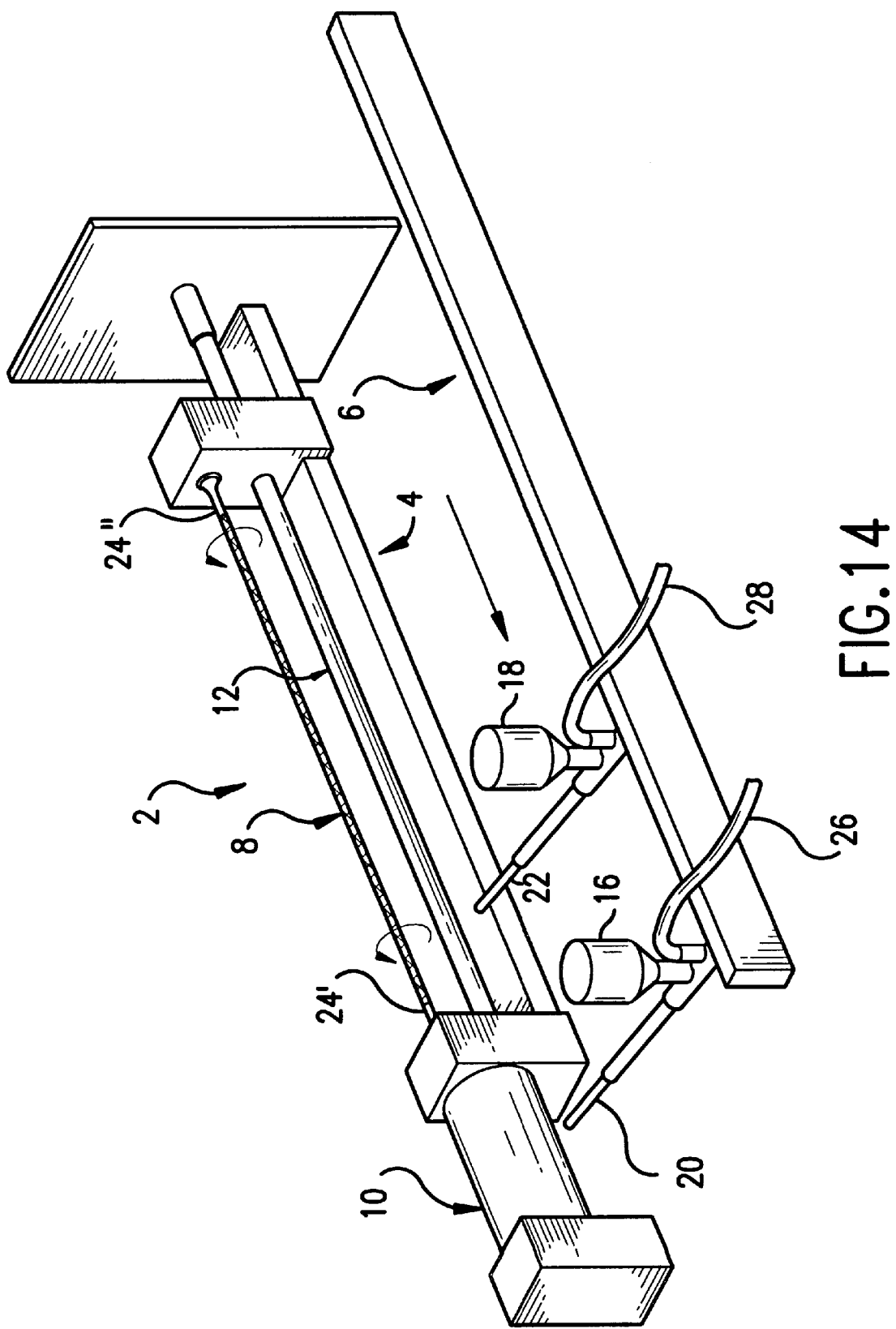

FIGS. 13 and 14 sequentially illustrate a different embodiment of the present invention. The reference numerals in this embodiment have the same meaning as those in the previous embodiment shown in FIGS. 11 and 12.

The first and second spray canisters 16, 18 can be mounted on structural support 14 on two tracks (not shown) to enable longitudinal movement back and forth. In this embodiment, canisters 16, 18 can move to and from independent from one another. In FIG. 13, the solid arrow shows the first canister 16 moving to the left and spraying the stent, while the hollow arrow indicates second canister 18 in a stationary position with the potential to move to the left. First canister 16 continues to the left and then stops beyond the stent and assumes a stationary position (not shown). 15 Then, as shown in FIG. 14, the second canister 18 moves to the left to spray the stent and then rests to the left of the stent. Thereafter, the first canister 16 can move to the right, later followed by the second canister 18, and the process can be repeated as desired.

Other processes according to this invention can include the first canister 16 going to and from while the second canister 18 is at rest beyond the stent, followed by the second canister going to and from while the first canister 16 is at rest beyond the stent. Other non-limiting variations include having canisters 16 and 18 move simultaneously but spaced apart from one another, or having canisters 16 and 18 criss-cross while spraying.

In addition to spray coating, the coatings of this invention can be applied by dipping the medical device in 1) a polymer dissolved in a first solvent and 2) a drug dissolved in a second solvent. The device can be repeatedly dipped into the polymer solution and drug solution until a coating of the desired thickness is achieved. In general, the polymer will shrink and swell, and the drug will recrystallize or redistribute in the subsequent dipping steps depending upon the relative solvability of the solvents to the polymer and drug. In order to ensure uniformity of the coating on the device, certain steps can be taken. These steps include, without limitation: choosing a solvent with a low viscosity index, choosing a polymer above its entanglement molecular weight such that the inner polymer layer(s) will swell but will not be easily dissolved, blow drying the coating after each dipping, horizontally coating the device, rotating the device during drying and using short coating times.

The following examples illustrate embodiments of the invention which were prepared by dipping.

EXAMPLE 4

15 grams of a silicone dispersion from Applied Silicone Corp. (#40000), containing 35% solids, was weighed. 0.52 grams of dexamethasone (DEX) (Upjohn, Lot #719kT) was dissolved in 15 mL of tetrahydrofuran (THF). The drug solution was added to the silicone dispersion and stirred until a homogeneous solution was formed.

A stent graft (Example 4a) was dipped into the solution and air dried in its horizontal position. The coating weight for this sample was 10.8 mg/cm$^2$. Due to gravity, the coating became uneven. To obtain a more uniform coating, a second stent graft (Example 4b), after being dipped into the solution, was rotated horizontally as it air dried. The coating weight for this sample was 13.5 mg/cm$^2$. After sitting at room temperature for about 1.5 hours, the coated samples were oven cured at 150° C. for 1 hour.

Figure 16:
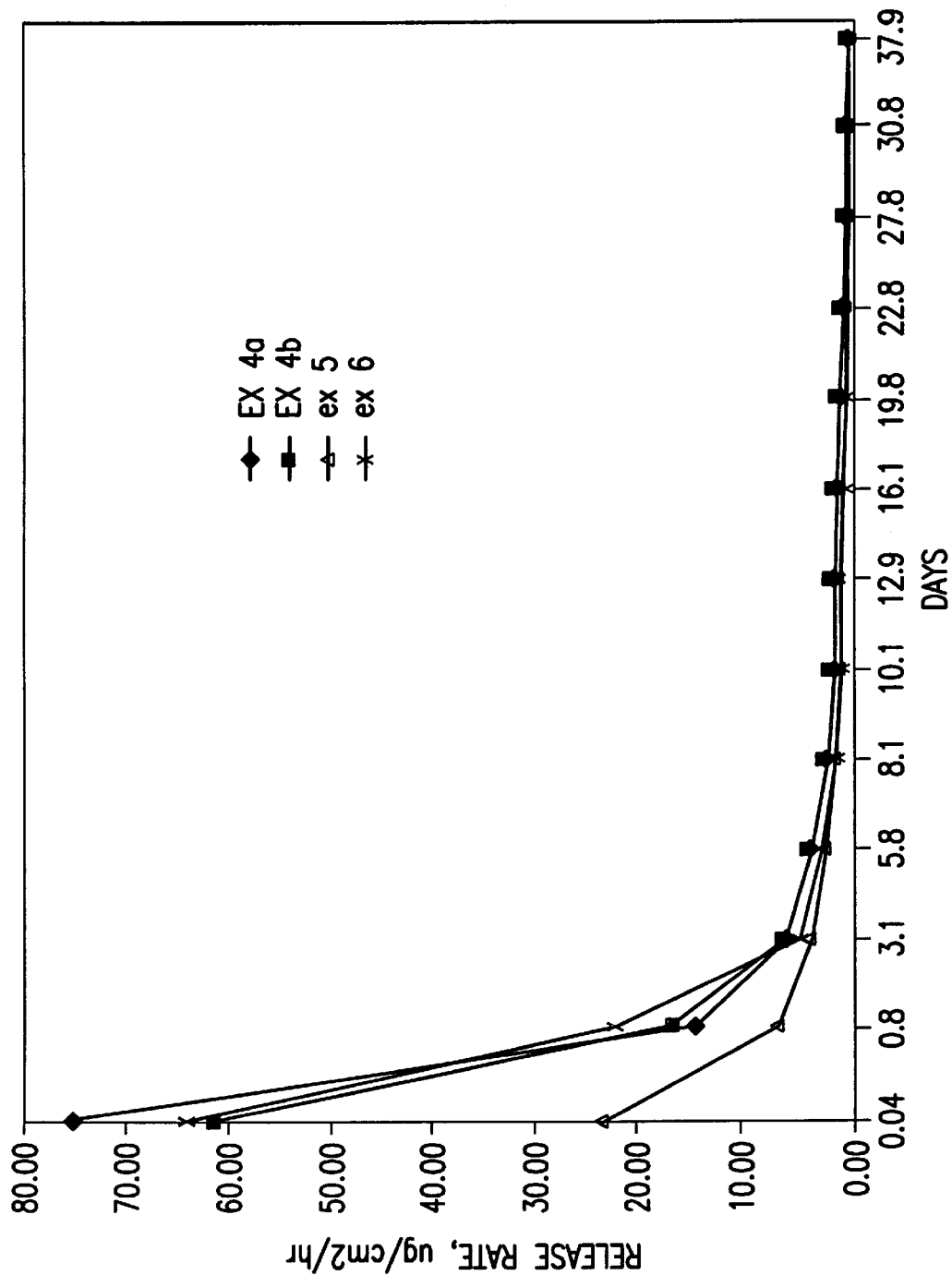
FIG. 16 is a graphical comparison of the elution rates of Examples 4a, 4b, 5 and 6.

The grafts were cut into 2 cm pieces and their release rates were studied by immersing the pieces in a 25/75 v/v aqueous solution of polyethylene glycol (PEG) (MW=400 from J. T. Baker). The solutions were periodically sampled and replaced with fresh solution. The amount of DEX released was quantified by a Shimadzu High Performance Liquid Chromatography (HPLC), using a C8 column (Phase Separation Ltd) with a mobile phase of acetonitrile/H$_2$O (1:1 v/v), a flow rate of 1 ml/min and a UV detector at a wavelength of 254 nm. The release rates for these two samples are presented in Table 2. The data shows that the coated samples can provide prolonged drug release (see FIG. 16).

TABLE 2

Release Rate Data ($\mu$g/cm$^2$/hr)

| Time (days) | Ex. 4a | Ex. 4b | Ex. 5 | Ex. 6 |
| --- | --- | --- | --- | --- |
| 0.0 | 75.26 | 61.51 | 23.66 | 63.96 |
| 0.8 | 14.54 | 16.80 | 6.68 | 22.14 |
| 3.1 | 5.75 | 6.55 | 3.71 | 4.76 |
| 5.8 | 3.46 | 3.97 | 2.31 | 2.19 |
| 8.1 | 2.02 | 2.65 | 1.61 | 1.27 |
| 10.1 | 1.64 | 2.22 | 1.27 | 0.85 |
| 12.9 | 1.48 | 2.02 | 1.34 | 1.41 |
| 16.1 | 1.48 | 1.94 | 1.25 | 1.59 |
| 19.8 | 1.30 | 1.81 | 1.12 | 0.71 |
| 22.8 | 1.05 | 1.45 | 0.96 | 0.57 |
| 27.8 | 0.89 | 1.29 | 0.83 | 0.46 |
| 30.8 | 0.81 | 1.16 | 0.72 | 0.47 |
| 37.9 | 0.70 | 1.05 | 0.65 | 0.33 |

EXAMPLE 5

A silicone dispersion containing 4% silicone in THF was prepared. Also prepared was a 10% solution of DEX in THF. A stent graft was dipped into the silicone solution first and dried while being rotated for at least 1 minute. The stent was then dipped into the DEX/THF solution and rotated for at least 1 minute to dry the stent. This sequence of dipping and drying was repeated for about 20 times. The last dip was in the silicone solution. After sitting at room temperature for about 1.5 hours, the coated samples were oven cured at 150° C. for 1 hour.

Like the stents in Example 4a and 4b, this sample was also cut into 2 cm pieces and the release rate was studied according to the procedure used in Examples 4a and 4b. The release rate for Example 5 is presented in Table 2 and FIG. 16. The data shows that the coated samples can provide prolonged drug release.

EXAMPLE 6

The silicone dispersion of Example 5 was prepared. Also prepared was a 10% solution of DEX in methanol (MeOH), which is a poor solvent for silicone and hence incompatible to silicone. A stent graft was coated according to the method used to prepared Example 5. This sample was cut into 2 cm pieces and the release rate was studied according to the procedure used in Examples 4a and 4b. The release rate for Example 6 is presented in Table 2. The data shows that the coated samples can provide prolonged drug release although this sample exhibited a faster initial drug elution rate than Examples 4a, 4b and 5 (see FIG. 16).

The description contained herein is for purposes of illustration and not for purposes of limitation. Changes and modifications may be made to the embodiments of the description and still be within the scope of the invention. Furthermore, obvious changes, modifications or variations will occur to those skilled in the art.

I claim:

1. A method of making a medical device having at least a portion for insertion or implantation into the body of a patient, wherein the portion has a surface which is adapted for exposure to body tissue of the patient and wherein at least a part of the surface is covered with a coating comprising at least one layer, to release at least one biologically active material therefrom, the method comprising:

a) applying a thermodynamically stable polymer system substantially free of a biologically active material comprising a polymer and a first solvent of the polymer to the surface, and b) applying a drug system substantially free of any polymer comprising a biologically active material and a second solvent of the biologically active material to the surface; wherein said method forms a substantially homogenous composite layer of the polymer and the biologically active material.

2. The method of claim 1 wherein steps (a) and (b) are repeated.

3. The method of claim 1 wherein the medical device is a stent.

4. The method of claim 1 wherein the stent is a self-expanding stent.

5. The method of claim 1 wherein the first solvent and second solvent are the same.

6. The method of claim 1 wherein the first solvent and second solvent are different.

7. The method of claim 1 wherein the polymer is a hydrophobic biostable elastomer.

8. The method of claim 7, wherein the elastomer is selected from the group consisting of silicones, polyurethanes, thermoplastic elastomers, ethylene vinyl acetate copolymers, polyolefin elastomers, EPDM rubbers and polyamide elastomers.

9. The method of claim 1 wherein the biologically active material is selected from the group consisting of antithrobotics, anticoagulants, antiplatelet agents, thrombolytics, antiproliferatives, anti-inflammatories, agents that inhibit hyperplasia, smooth muscle cell inhibitors, antibiotics, growth factors, growth factor inhibitors, cell adhesion inhibitors, cell adhesion promoters and drugs that enhance the formation of healthy neointimal tissue.

10. The method of claim 1 wherein the polymer system or drug system is applied by spray coating.

11. The method of claim 1 wherein the polymer system or drug system is applied by dipping.

12. The method of claim 1 wherein the polymer system and the drug system are applied simultaneously to the surface.

13. The method of claim 1 wherein the polymer system and the drug system are applied sequentially to the surface.

14. The method of claim 1 which further comprises partially evaporating the first solvent prior to applying the drug system.

15. The method of claim 1 wherein the biologically active material is dissolved in the second solvent.

16. The method of claim 1 wherein the biologically active material is suspended in the second solvent.

17. The method of claim 1 which further comprises applying a solvent system to the coating layer.

18. The method of claim 1 which further comprises applying a second drug system substantially free of a polymer comprising a second biologically active material to the surface.

* * * * *